US00PP31617P3

(12) United States Plant Patent
Kleynhans

(10) Patent No.: US PP31,617 P3
(45) Date of Patent: Mar. 31, 2020

(54) ***LACHENALIA* JACQ. F. EX MURRAY PLANT NAMED 'JOSEPHINE'**

(50) Latin Name: ***Lachenalia* Jacq. f. ex Murray**
Varietal Denomination: Josephine

(71) Applicant: AGRICULTURAL RESEARCH COUNCIL, Pretoria (ZA)

(72) Inventor: Riana Kleynhans, Benoni (ZA)

(73) Assignee: Agricultural Research Council, Pretoria (ZA)

( * ) Notice: Subject to any disclaimer, the term of this patent is extended or adjusted under 35 U.S.C. 154(b) by 0 days.

(21) Appl. No.: 14/756,802

(22) Filed: Oct. 15, 2015

(65) Prior Publication Data

US 2017/0112036 P1 Apr. 20, 2017

(51) Int. Cl.
*A01H 5/02* (2018.01)
*A01H 6/12* (2018.01)

(52) U.S. Cl.
USPC ..... Plt./263.1
CPC ..... *A01H 6/12* (2018.05)

(58) Field of Classification Search
USPC ..... Plt./263.1
See application file for complete search history.

(56) References Cited

PUBLICATIONS

UPOV hit on *Lachenalia* plant named 'Josephine', ZA PBR ZA20104394, granted 2010.*
ARC*LNR *Lachenalia* and other Flower bulb cultivars at the ARC, R. Kleynhans and S. Venter, Jul. 2012, pp. 1-23.*
Guidelines for the conduct of tests for distinctness, homogeneity and stability, *Lachenalia,* UPOV TG/126/4, published Oct. 12, 1990, downloaded from http://www.upov.int/en/publications/tg-rom/tg126/tg_126_4.pdf on Jan. 12, 2018 (Year: 1990).*
CPVO Variety Data Sheet for Application No. 20141911, Applicant: Agricultural Research Council, Application/Filing Date Jul. 29, 2014, published Oct. 15, 2014, 1 page, Community Plant Variety Office, France.
Certificate of Grant of Plant Breeder's Right, Registration No. ZA20104393, Applicant: ARC (Agricultural Research Council), dated Apr. 20, 2010, 1 page, Department Agriculture Forestry and Fisheries, Republic of South Africa.
CPVO Variety Data Sheet for Application No. 20141910, Applicant: Agricultural Research Council, Application/Filing Date Jul. 29, 2014, published Dec. 15, 2014, 1 page, Community Plant Variety Office, France.
Certificate of Grant of Plant Breecler's Right, Registration No. ZA20104392, Applicant: ARC (Agricultural Research Council), dated Apr. 20, 2010, 1 page, Department of Agriculture Forestry and Fisheries, Republic of South Africa.
CPVO Variety Data Sheet for Application No. 20141912, Applicant: Agricultural Research Council, Application/Filing Date Jul. 29, 2014, published Oct. 15, 2014, 1 page, Community Plant Variety Office, France.
Certificate of Grant of Plant Breeder's Right, Registration No. ZA20104394, Applicant: ARC (Agricultural Research Council), dated Apr. 20, 2010, 1 page, Department of Agriculture Forestry and Fisheries, Republic of South Africa.
CPVO Variety Data Sheet for Application No. 20141915, Applicant: Agricultural Researth Council, Application/Filing Date Jul. 29, 2014, published Dec. 15, 2014, 1 page, Community Plant Variety Office, France.
Certificate of Grant of Plant Breeder's Right, Registration No. ZA20104396, Applicant: ARC (Agricultural Research Council), dated Apr. 20, 2010, 1 page, Department of Agriculture Forestry and Fisheries, Republic of South Africa.
CPVO Variety Data Sheet for Application No. 20141914, Applicant: Agricultural Research Council, Application/Filing Date Jul. 29, 2014, published Dec. 15, 2014, 1 page, Community Plant Variety Office, France.
Certificate of Grant of Plant Breeder's Right, Registration No. ZA20104397, Applicant: ARC (Agricultural Research Council), dated Apr. 20, 2010, 1 page, Department Agriculture Forestry and Fisheries, Republic of South Africa.
CPVO Variety Data Sheet for Application No. 20141913, Applicant: Agricultural Research Council, Application/Filing Date Jul. 29, 2014, published Dec. 15, 2014, 1 page, Community Plant Variety Office, France.
Certificate of Grant of Plant Breeder's Right, Registration No. ZA20104395, Applicant: ARC (Agricultural Research Council), dated Apr. 20, 2010, 1 page, Department of Agriculture Forestry and Fisheries, Republic of South Africa.
Co-Pending U.S. Appl. No. 14/756,801, inventor Kleynhans, R., filed Oct. 15, 2015 (Not Published).
Co-Pending U.S. Appl. No. 14/756,803, inventor Kleynhans, R., filed Oct. 15, 2015 (Not Published).
Co-Pending U.S. Appl. No. 14/756,821, inventor Kleynhans, R., filed Oct. 19, 2015 (Not Published).
Co-Pending U.S. Appl. No. 14/756,819, inventor Kleynhans, R., filed Oct. 19, 2015 (Not Published).
Co-Pending U.S. Appl. No. 14/756,820, inventor Kleynhans, R., filed Oct. 19, 2015 (Not Published).
Niederwieser, J.G., and Vcelar, B., "Regeneration of *Lachenalia* Species from Leaf Explants," *HortScience 25*(6):684-687, American Society for Horticultural Science, United States (1990).
Slabbert, M.M. and Niederwieser, J.G., "In vitro bulblet production of *Lachenalia," Plant cell Reports 18:*620-624, Springer-Verlag, Germany (1999).

* cited by examiner

*Primary Examiner* — Anne Marie Grunberg
(74) *Attorney, Agent, or Firm* — Sterne, Kessler, Goldstein & Fox P.L.L.C.

(57) ABSTRACT

A new and distinct form of *Lachenalia* plant characterized by a bulb plant type having a spreading growth habit of a height of 15-30 centimetres (cm) and width of 10-15 cm; a hyacinth-like yellow flower with maroon tip which displays very compact inflorescence; and further having a lanceolate leaf form.

2 Drawing Sheets

*LACHENALIA* JACQ. F. EX MURRAY PLANT NAMED 'JOSEPHINE'

Genus and species: *Lachenalia* Jacq. f. ex Murray.
Variety denomination: 'Josephine'.

BACKGROUND OF THE INVENTION

The present invention relates to a new and distinct cultivar of *Lachenalia*, botanically known as *Lachenalia* Jacq. f. ex Murray having the common name of Viooltjies/Cape cowslip and hereinafter referred to by its variety denomination 'Josephine'.

The variety was first cultivated in 2008 and originated by means of conventional breeding by the inventor during 2009 to 2010 at the premises of Agricultural Research Council Vegetable and Ornamental Plant Institute, Roodeplaat, Pretoria, Republic of South Africa.

Asexual reproduction of the 'Josephine' plant at the same location has shown that the unique features thereof are stable and reproduced true to type in successive generations of asexual reproduction.

SUMMARY OF THE INVENTION

The present invention constitutes a new and distinct variety of *Lachenalia* which originated from the controlled pollination between a *Lachenalia* hybrid as seed bearing parent and a *Lachenalia* hybrid as pollen parent as detailed hereinbelow.

The following traits have been repeatedly observed and are determined to be the unique characteristics, under the local evaluation conditions, of the 'Josephine' plant. These characteristics in combination distinguish 'Josephine' as a new and distinct *Lachenalia* cultivar:

1. Bulb plant type having a spreading growth habit of a height of 15-30 centimetres (cm) and width of 10-15 cm.
2. Flower color: yellow (RHS #9B) with maroon (RHS #53B) tip.
3. Leaf form: Lanceolate.
4. Flower form: Hyacinth like. Infloresence very compact.

Color references are made to The R.H.S. Colour Chart, 1st edition, 1966, except where general color terms of ordinary significance are used or indicated otherwise.

Plants of the new *Lachenalia* variety 'Josephine' can be compared to similar denominations such as 'Romaud' and 'Namakwa' but differs in that the flower color and leaf form of 'Romaud' is greenish yellow and oval respectively; and that the flower form of 'Namakwa' is tubular with the inflorescence of the 'Namakwa' not being compact.

'Romaud' is scented, whereas 'Josephine' is not. The flower color of 'Josephine' is more yellow (RHS #9B) with maroon (RHS #53B) tips with a clear green-yellow (RHS #154A) tip of the outer perianth apex segment compared to the more greenish yellow colour of 'Romaud'. 'Romaud' also does not have the maroon tips on the flowers. Both 'Josephine' and 'Romaud' has compact inflorescence with many flowers although 'Josephine' naturally grows shorter and are thus well suited for pot plant production.

Although 'Namakwa' also has yellow flowers with reddish tips, the flower orientation differs and the inflorescence are not nearly as compact as 'Josephine'. The yellow colour of 'Namakwa' is also brighter than that of 'Josephine'. 'Namakwa' has longer more tubular flowers (tips not recurving) compared to the shorter more campanulate flowers (tips recurving) of 'Josephine'. The flowers of 'Namakwa' have a horizontal to slightly hanging orientation compared to the horizontal orientation of 'Josephine'. These differences lead to a much more compact inflorescence of 'Josephine' compared to 'Namakwa'. 'Namakwa' tends to extend a longer peduncle again contributing to a much less compact growth form compared to 'Josephine'.

'Josephine' thus has the brighter colours of 'Namakwa' but the more compact growth form of 'Romaud'.

BRIEF DESCRIPTION OF THE DRAWINGS

The first drawing illustrates the overall appearance of the 'Josephine', showing the colors as true as it is reasonably possible to obtain in colored reproductions of this type. The first drawing comprises a front perspective view of a typical 'Josephine' grown in an indoor nursery.

The second drawing illustrates the overall appearance of the 'Josephine', showing the colors as true as it is reasonably possible to obtain in colored reproductions of this type. The second drawing comprises a front perspective view of a typical 'Josephine' grown in an indoor nursery.

DETAILED DESCRIPTION

The aforementioned drawings, following observations and measurements describe 'Josephine' grown by the inventor on behalf of Agricultural Research Council Vegetable and Ornamental Plant Institute, Roodeplaat, Pretoria, Republic of South Africa. Thereafter 'Josephine' was made subject of a South African Plant Breeders' Right application in March 2009. This application was granted in 2010 under number ZA20104394.

The plant may be used for landscaping and should be planted during the month of March; indoors and in pots only. The plant should be kept at temperatures of 20-25 degrees Celsius during the day and 10-15 degrees Celsius at night. Plenty of light should be provided.

'Josephine' is a naturally short hyacinth-like cultivar. It is early to intermediate flowering and has an excellent keeping quality.

'Josephine' is a hybrid-hybrid cross containing the following *Lachenalia* species: *Lachenalia orchioides* subsp. *glaucina, Lachenalia bulbifera, Lachenalia quadricolor, Lachenalia aloides.*

The specific 'Josephine' parentage is as follows:

Female parent has the following crossing history—([*L. aloides* x *L. rubida*] x [*L. aloides* x *L. rubida*]) x (*L. aloides* x *L. aloides*)

Male parent has the following crossing history—([L. *orchioides* x *L. aloides*] x [*L. orchioides* x *L. aloides*]).

The female parent (GenBank accession number 1994/153/021) has greener flowers, but with the same flower orientation and compact growth as 'Josephine'. The male parent (GenBank accession number 1993/116/003) is a *Lachenalia aloides* intra species hybrid with plain bright yellow hanging bell shaped flowers, with widely recurving tips. The male parent is fairly compact, but very different from the more hyacinth-like inflorescence of 'Josephine'. The male parent has plain yellow flowers whereas 'Josephine' has the combination colored flowers (yellow (RHS #9B) and maroon (RHS #53B)). The flower orientation is also clearly different, with 'Josephine' having more horizontal flowers and the male parent having hanging flowers. Flowers of the male parent are longer than those of 'Josephine'.

'Josephine' was originally produced sexually from a cross between the two hybrids mentioned above. A specific seedling with number 2000/40/93 was selected from this cross and thereafter asexually propagated. The asexual progeny of this seedling is the cultivar 'Josephine' and was multiplied via tissue culture at the premises of Agricultural Research Council Vegetable and Ornamental Plant Institute, Roodeplaat, Pretoria, Republic of South Africa.

The following characteristics of 'Josephine' are described with reference to description of said characteristic which are comparable with the mentioned variety/ies having said similar characteristic.

Leaf: Monocolored.

| Characteristic: | Description of 'Josephine': | Variety having similar characteristics: |
|---|---|---|
| Attitude | Semi-erect | 'Romaud' |
| Length | Long: 14.6 cm | 'Lizette', 'Romaud', 'Romelia' |
| Width | Medium: 2.4 cm | 'Rosabeth' |
| Ratio length:width | Medium: 6:1 | 'Romaud' |
| Shape | Lanceolate | 'Rodelein' |
| Color | Light green (RHS #141C) | 'Romelia' |
| Leaf color designation for lower sides of the leaf | Light green (RHS #141C) | |
| Shape in cross-section | Angular | 'Robyn', 'Romelia' |
| Recurving of margin | Present | 'Romaud' |
| Undulation of margin | Absent | 'Romelia' |
| Pubescence of upper side | Absent | 'Rodelein', 'Rosabeth' |
| Blistering of upper side | Absent | 'Rodelein', 'Rosabeth' |
| Spots on upper side | Present | 'Bontrok; 'Roinge', 'Rosabeth' |
| Number of spots per leaf | Amount differs from plant to plant, no exact number of spots per leaf | |
| Color of spots on upper side | Greenish (RHS #138A) | |
| Size of spots on upper side | Medium (2-3 millimeter (mm)) | 'Robyn', 'Roinge' |
| Density of spots on upper side | Medium | 'Roinge', 'Rosabeth' |
| Intensity of color of spots on upper side | Light | 'Romaud' |
| Markings on outer side of leaf base | Absent | 'Rodelein' |

Peduncle:

| Characteristic: | Description of 'Josephine': | Variety having similar characteristics: |
|---|---|---|
| Length | Short (15 cm) | 'Rolene', Romaud' |
| Peduncle color designation | Purplish (RHS #53B) with green (RHS #141D) | |
| Spots or markings | Present | 'Bontrok; 'Rosabeth' |
| Coloration of peduncle spots | Green (RHS #141D) | |
| Size of spots or markings | Medium (2-3 mm) | 'Robyn' |
| Density of spots or markings | Sparse, close to each other: spots may be as close as 0.2 mm, but may differ | 'Robekkie' |

Bud:

| Characteristic: | Description of 'Josephine': |
|---|---|
| Color | Pink (RHS #67C) |

Inflorescence:

| Characteristic: | Description of 'Josephine': | Variety having similar characteristics: |
|---|---|---|
| Length | Short (12 cm) | 'Bontrok' |
| Rudimentary apex | Inconspicuous | 'Rosabeth' |
| Number of flowers | Many (40+ flowers) | 'Romaud', 'Sonni' |

Flower:

| Characteristic: | Description of 'Josephine': | Variety having similar characteristics: |
|---|---|---|
| Description of floral organs | Inflorescence containing individual bell-shaped flowers attached with pedicels to the peduncle | |
| Predominant color: | Yellow (RHS #9B) | 'Romaud', 'Ronette' |
| Intensity of predominant color: | Strong | 'Romelia', 'Winseme' |
| Inner perianth segment: color of margin of apex relative to other part | Clearly different | 'Louis', 'Roinge' |
| Attitude: | Horizontal to pendulous | |
| Flower length: | Short: 1.9 cm | 'Rodelein' |
| Pedicel: | Present | 'Romelia' |
| Pedicel length: | Medium (2-3 mm) | 'Bontrok; 'Louis' |
| Flower diameter excluding apex: | Small to medium: 0.6 cm | |
| Flower diameter at apex: | Medium: 1.3 cm | 'Ronita' |
| Flower attitude of distal part of inner perianth segments: | Spreading | 'Rozanne' |
| Flower glossiness: | Absent | |
| Outer perianth segment: color of basal part just before opening of flower: | Yellow (RHS #9C of RHS color chart, 2nd edition, 1986) | |
| Outer perianth segment: color of basal part of fully opened flower: | Yellow (RHS #13A of RHS color chart, 2nd edition, 1986) | |
| Outer perianth segment: color of apex relative to other part: | Clearly different | 'Ronette' |
| Outer perianth segment: color of apex relative to other part: | Green-yellow (RHS #154A) | 'Bontrok; Leipoldt, 'Roinge' |
| Inner perianth segment: distinct spot in middle of apex: | Absent | 'Bontrok' |
| Inner perianth segment: color of margin of apex relative to other part: | Clearly different | 'Louis', 'Roinge' |
| Inner perianth segment: color of margin of apex relative to other part: | Pale purple (RHS #61C) | 'Rozanne' |
| Inner perianth segment: predominant color of exposed part (excluding differently colored margin of apex) | Yellow (RHS #9A of RHS color chart, 2nd edition, 1986) | |
| Length of inner perianth segment compared to outer segments | Longer | 'Roinge', 'Rosabeth' |
| Extrusion of stamens | Present | 'Louis', 'Rolene' |
| Fragrance | Absent | 'Romelia' |
| Bulb: predominant shape | Oblate | 'Romaud' |
| Time of flowering | Early - flowering time vary from May to June (Southern Hemisphere) | 'Celia', 'Lizelle', 'Sonni' |

-continued

| Characteristic: | Description of 'Josephine': | Variety having similar characteristics: |
|---|---|---|
| Duration of flowering | Long (up to 2 months) | 'Romelia', 'Rosabeth' |

Others:

| Characteristic: | Description of 'Josephine': |
|---|---|
| Description of the bulb including size and color of the bulb at maturity | Cream/white (color designation - RHS #158B)<br>Size: between 1.5 to 2 cm in diameter |
| Time of leaf growth/bud burst | Starts within the first week of watering (normally March/April in Southern Hemisphere |
| A description of any fruit and seed set | No seed or fruit |
| Timing of leaf senescence | After flowering has completed and starts to die down, the leaves start to die off (wheat color) and plant dry out (September-October in Southern Hemisphere) |

The variety is not genetically modified and has been tested to be free of Ornithogalum Mosaic Virus.

The invention claimed is:

1. A new and distinct variety of *Lachenalia* plant named 'Josephine' as illustrated and described herein.

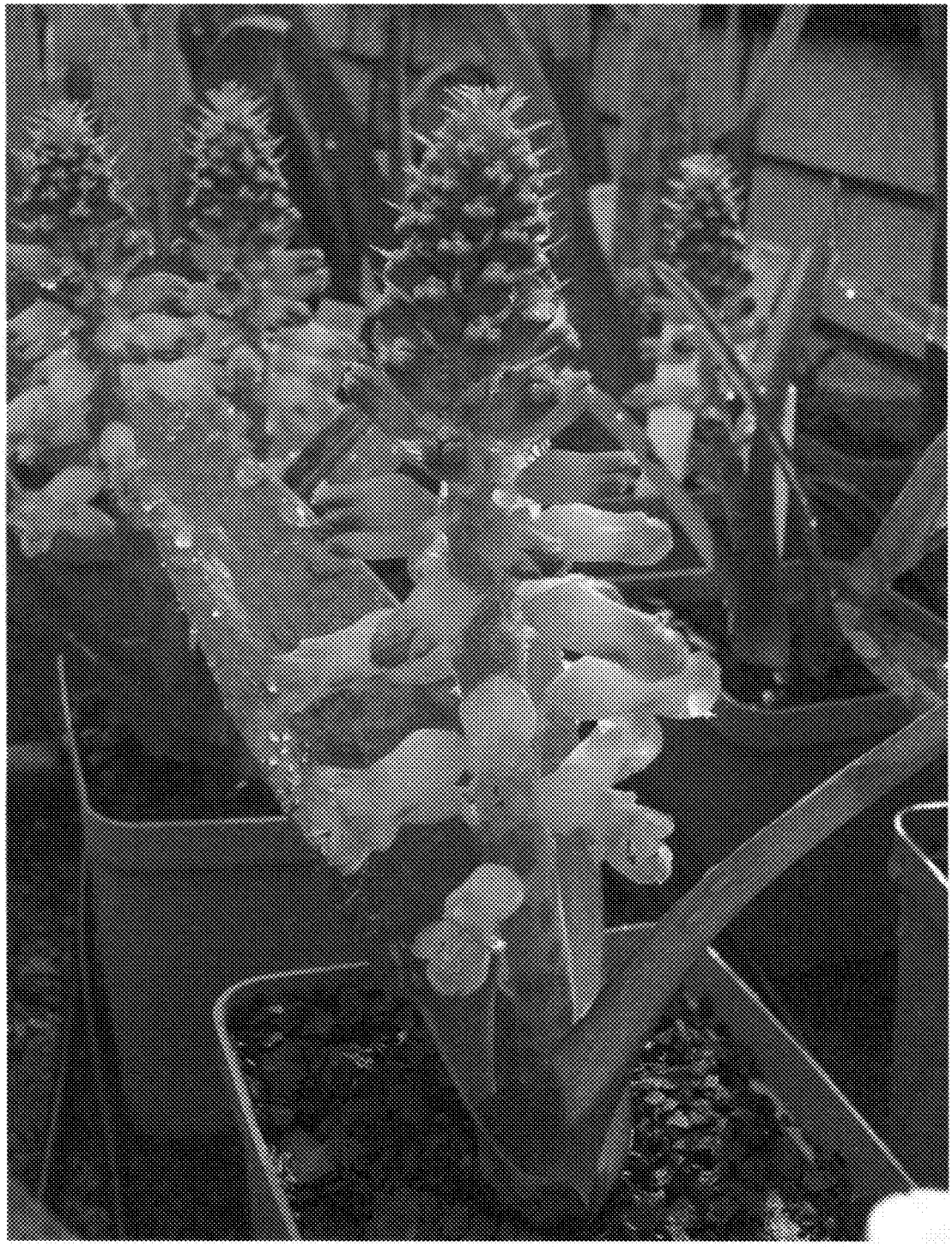

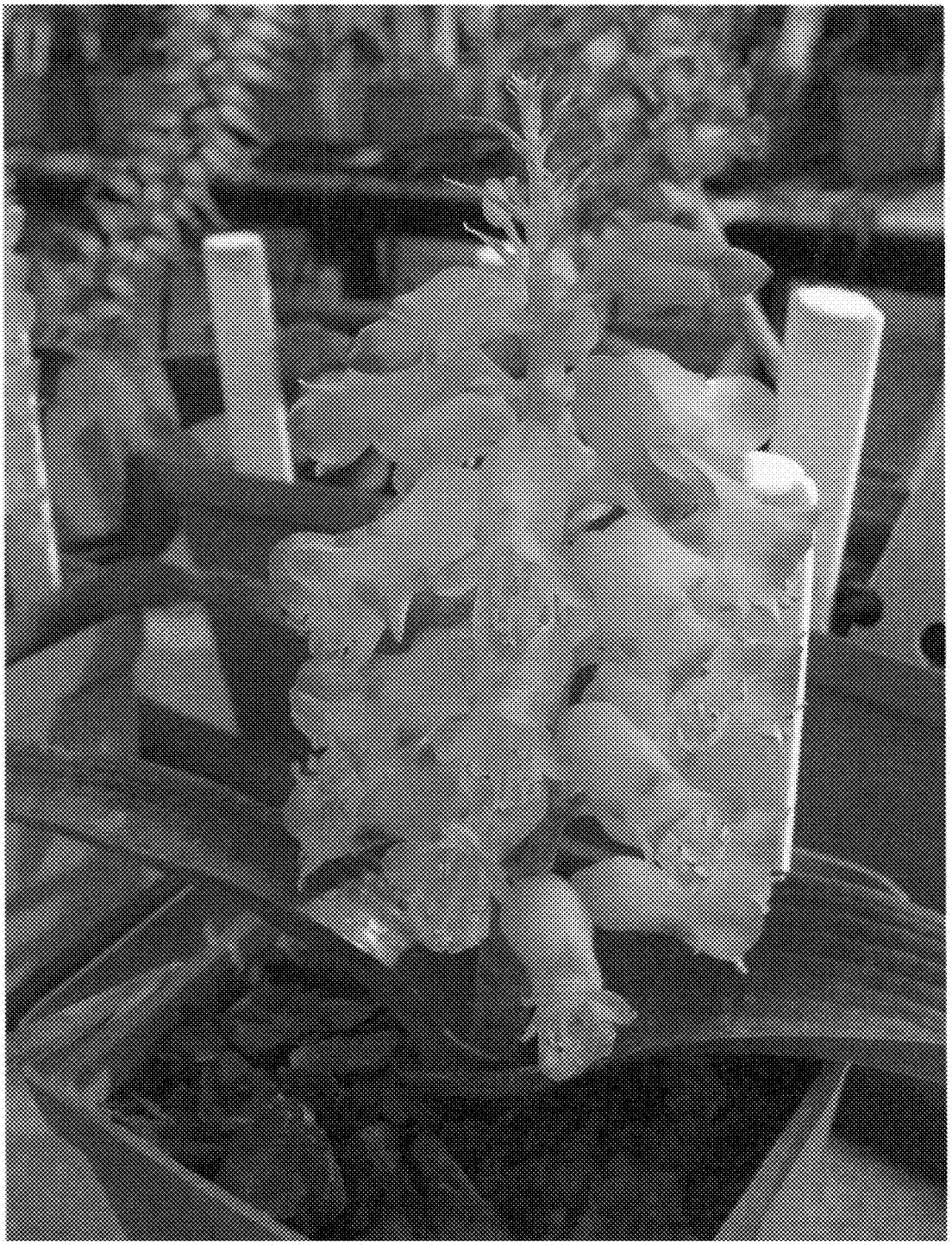

* * * * *